(12) United States Patent
Young

(10) Patent No.: US 11,284,981 B2
(45) Date of Patent: Mar. 29, 2022

(54) TOOTH WHITENING SYSTEM AND METHOD

(71) Applicant: KONINKLIJKE PHILIPS N.V., Eindhoven (NL)

(72) Inventor: Nigel David Young, Surrey (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 11 days.

(21) Appl. No.: 15/521,690

(22) PCT Filed: Oct. 2, 2015

(86) PCT No.: PCT/EP2015/072785
§ 371 (c)(1),
(2) Date: Apr. 25, 2017

(87) PCT Pub. No.: WO2016/066370
PCT Pub. Date: May 6, 2016

(65) Prior Publication Data
US 2017/0231735 A1  Aug. 17, 2017

(30) Foreign Application Priority Data
Oct. 29, 2014  (EP) .................................... 14190829

(51) Int. Cl.
*A61C 19/06* (2006.01)
*A61C 13/15* (2006.01)
(Continued)

(52) U.S. Cl.
CPC ........ *A61C 19/066* (2013.01); *A61B 1/00006* (2013.01); *A61B 1/00009* (2013.01);
(Continued)

(58) Field of Classification Search
CPC ....... A61C 19/066; A61C 5/90; A61C 19/003; A61C 9/0053; A61B 1/00006;
(Continued)

(56) References Cited

U.S. PATENT DOCUMENTS

| 4,952,143 A * | 8/1990 | Becker ...................... A61C 5/00 |
| | | 433/215 |
| 8,801,763 B2 | 8/2014 | Fish et al. |

(Continued)

FOREIGN PATENT DOCUMENTS

| CN | 201404306 Y | 2/2010 |
| CN | 102764163 A | 11/2012 |

(Continued)

OTHER PUBLICATIONS

"DentalSMILE"; Brochure From Dental Smile Pattaya, 3 Page Document, Downloaded From http://www.dentalsmilepattaya.com/toothwhitening.html on Aug. 1, 2013.

(Continued)

*Primary Examiner* — Nicholas D Lucchesi
*Assistant Examiner* — Hao D Mai

(57) ABSTRACT

A smart lighting system for applying light to teeth in the context of tooth whitening and teeth that have been provided with a light-curable whitening varnish. The system includes a light-generating unit, a light-patterning unit, a mouth imaging unit, a mouth image sensing unit, and an image processing and control unit, and is adapted so as to allow the image processing and control unit to adjust the light-patterning unit on the basis of information obtained from the mouth image sensing unit. By doing so, prior to allowing the light-generating unit to emit light, it can be ensured that light emitted to assist tooth whitening, does not affect soft tissue.

4 Claims, 2 Drawing Sheets

(51) Int. Cl.
| | |
|---|---|
| *A61N 5/06* | (2006.01) |
| *A61C 5/90* | (2017.01) |
| *A61B 1/04* | (2006.01) |
| *A61B 1/06* | (2006.01) |
| *A61B 1/24* | (2006.01) |
| *A61K 8/22* | (2006.01) |
| *A61K 8/41* | (2006.01) |
| *A61Q 11/00* | (2006.01) |
| *A61C 9/00* | (2006.01) |
| *A61B 1/00* | (2006.01) |

(52) U.S. Cl.
CPC ............... *A61B 1/04* (2013.01); *A61B 1/06* (2013.01); *A61B 1/24* (2013.01); *A61C 5/90* (2017.02); *A61C 19/003* (2013.01); *A61K 8/22* (2013.01); *A61K 8/41* (2013.01); *A61N 5/062* (2013.01); *A61N 5/0603* (2013.01); *A61N 5/0624* (2013.01); *A61Q 11/00* (2013.01); *A61C 9/0053* (2013.01); *A61K 2800/81* (2013.01); *A61N 2005/0606* (2013.01)

(58) Field of Classification Search
CPC ......... A61B 1/00009; A61B 1/04; A61B 1/06; A61B 1/24; A61K 8/22; A61K 8/41; A61K 2800/81; A61N 5/0603; A61N 5/062; A61N 5/0624; A61N 2005/0606; A61Q 11/00
See application file for complete search history.

(56) References Cited

U.S. PATENT DOCUMENTS

| | | | | |
|---|---|---|---|---|
| 9,662,284 | B2* | 5/2017 | Montgomery | A61K 8/22 |
| 2005/0100515 | A1* | 5/2005 | Sagel | A61C 19/063 |
| | | | | 424/53 |
| 2005/0186539 | A1* | 8/2005 | McLean | A61C 19/063 |
| | | | | 433/215 |
| 2005/0202363 | A1 | 9/2005 | Osterwalder | |
| 2005/0249677 | A1* | 11/2005 | Malcmacher | A61K 8/0208 |
| | | | | 424/53 |
| 2007/0276455 | A1* | 11/2007 | Fiset | A61C 19/066 |
| | | | | 607/91 |
| 2008/0280260 | A1 | 11/2008 | Belikov et al. | |
| 2009/0142724 | A1 | 6/2009 | Roosenblood et al. | |
| 2011/0223119 | A1* | 9/2011 | Isobe | A61K 8/345 |
| | | | | 424/57 |
| 2012/0251971 | A1* | 10/2012 | Fish | A46B 15/0002 |
| | | | | 433/27 |
| 2013/0323673 | A1* | 12/2013 | Hakomori | A61B 5/0261 |
| | | | | 433/29 |
| 2015/0164335 | A1* | 6/2015 | Van Der Poel | A61C 9/0053 |
| | | | | 433/29 |
| 2015/0305670 | A1* | 10/2015 | Spruit | A46B 15/0036 |
| | | | | 433/27 |
| 2016/0022389 | A1* | 1/2016 | Esbech | G01J 3/513 |
| | | | | 250/208.1 |
| 2016/0147002 | A1* | 5/2016 | Huang | G02B 6/0008 |
| | | | | 362/553 |

FOREIGN PATENT DOCUMENTS

| | | |
|---|---|---|
| CN | 202876118 U | 4/2013 |
| EP | 1457200 A1 | 9/2004 |
| EP | 2901964 A1 | 8/2015 |
| KR | 20140039462 A | 4/2014 |
| TW | 201225926 A | 7/2012 |
| WO | 0151005 A2 | 7/2001 |
| WO | 2006014370 A2 | 2/2006 |
| WO | 2008072803 A1 | 6/2008 |
| WO | 2011077299 A2 | 6/2011 |
| WO | 2014097053 A1 | 6/2014 |

OTHER PUBLICATIONS

Pretty et al: "Quantification of Dental Plaque in the Research Department"; Journal of Dentistry (2005) 33, pp. 193-207.
"Teeth Whitening Using the Whitening Strips Method Vs. Using the "Beyond Whitening" Accelerator—Comparative Research"; Silesian Center for Dental Implantology, 2010, 7 Page Document.

* cited by examiner

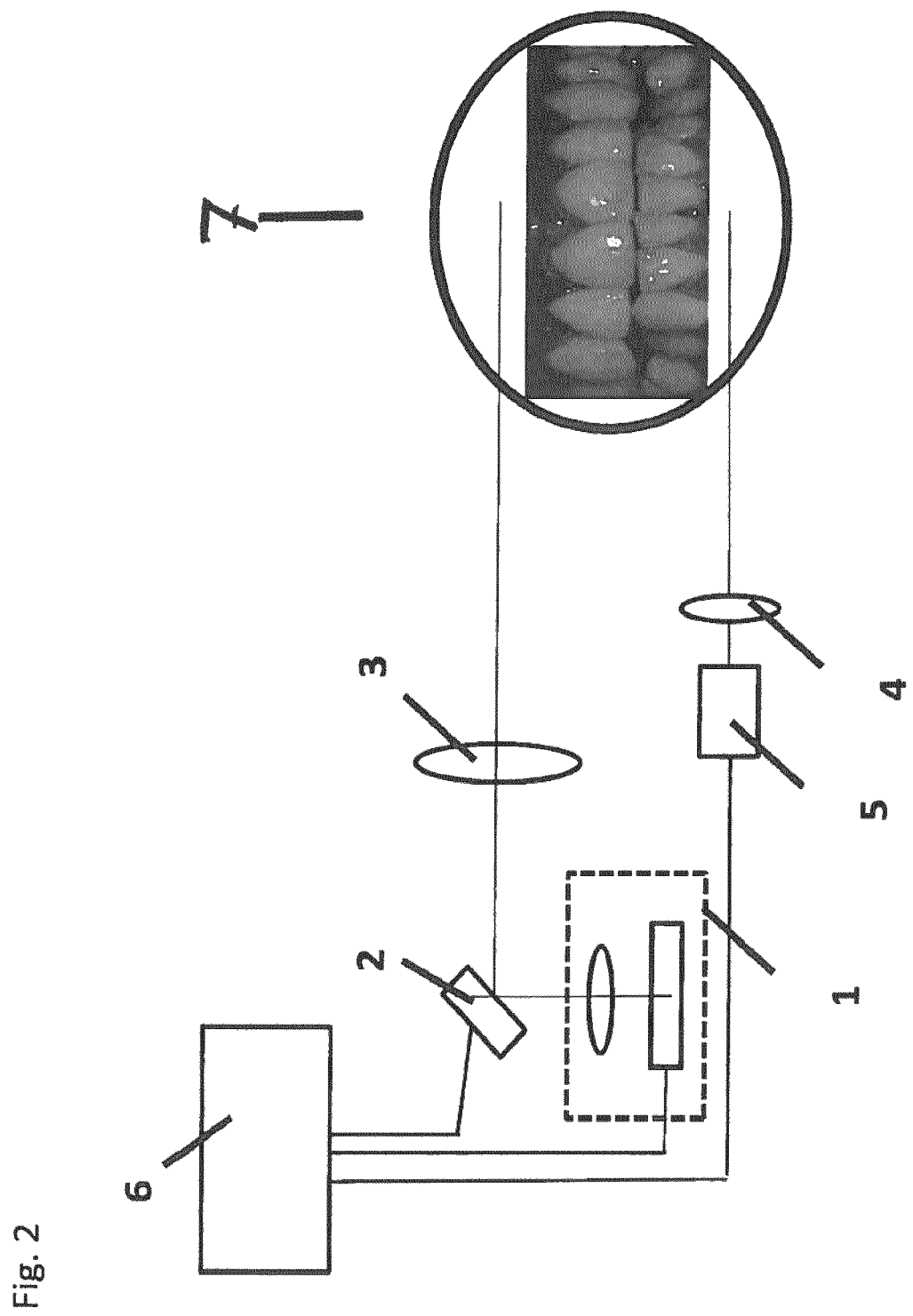

TOOTH WHITENING SYSTEM AND METHOD

CROSS-REFERENCE TO PRIOR APPLICATIONS

This application is the U.S. National Phase application under 35 U.S.C. § 371 of International Application No. PCT/EP2015/072785, filed on Oct. 2, 2015, which claims the benefit of European Patent Application, EP14190829.3, filed on Oct. 29, 2014. These applications are hereby incorporated by reference herein.

FIELD OF THE INVENTION

The invention relates to the dental care arts, and related arts and more specifically concerns a method for whitening teeth.

BACKGROUND OF THE INVENTION

Tooth whitening products that are based on hydrogen peroxide and other bleaching agents, such as carbamide peroxide and sodium percarbonate, include toothpastes, peroxide gel strips, whitening solutions, and mouthwashes. The aim is usually to deliver a whitening agent to the teeth in a sufficient amount to effect a colour change in the enamel and dentine of the teeth in an acceptable period of time without causing harm to the user. Some methods rely on using a high concentration (e.g., 25%) hydrogen peroxide gel applications often with light assistance for a short time (e.g., 4×15 minutes). Other methods use a much lower concentration of gel or varnish (e.g., 1-6% hydrogen peroxide) for a longer time (e.g., 5-40 hours, either in a single treatment or over several treatments) without high power light assistance. Care has to be taken when using high concentrations of hydrogen peroxide to avoid damage to soft tissue, such as the gums, and thus such methods are often regulated and are best employed by dental professionals. Peroxide gel strips use lower concentrations of hydrogen peroxide or carbamide peroxide, but entail wearing a plastic strip on the teeth to be treated for an extended period, or inserting fresh strips repeatedly over a long period.

In WO 2014/097053 a method of whitening teeth is disclosed, whereby a curable whitening varnish composition is applied. The composition comprises a matrix material having a bleaching agent dispersed therein. After application, the cured varnish composition is exposed to light energy to enhance the efficacy of the bleaching agent. The disclosed method avoids the potential damaging of soft tissue, by limiting the application of the whitening agent to the teeth, yet without the drawbacks associated with the application of the aforementioned peroxide gel strips.

However, even with the availability of a whitening varnish as disclosed in WO 2014/097053, tooth whitening using high concentrations of hydrogen peroxide with light assistance still require great care to avoid affecting soft tissue, if not by the peroxide, then by the light. It would therefore be desired, to provide a tooth whitening method that is altogether limited to the surface of the teeth only, yet allowing high concentrations of bleaching agent, and without the drawbacks of using strips.

SUMMARY OF THE INVENTION

In order to better address the foregoing desires, the invention, in one aspect, presents a system for applying light of a desired high intensity to teeth, the system comprising a light-generating unit (1), a light-patterning unit (2), a light projection unit (3), a mouth imaging unit (4), a mouth image sensing unit (5), and an image processing and control unit (6), wherein two or more of these units are optionally combined as a single component; the system being adapted so as to allow the image processing and control unit to adjust the light-patterning unit on the basis of information obtained from the mouth image sensing unit, prior to allowing the light-generating unit to emit light of the desired high intensity.

In another aspect, the invention provides a kit for the whitening of teeth, said kit comprising a system as described in the previous paragraph, and a supply of a curable whitening varnish comprising a bleaching agent.

In still another aspect, the invention concerns a non therapeutic method for light-activated tooth whitening comprising the steps of: applying a curable whitening varnish composition containing a bleaching agent to the surface of a tooth; curing the whitening varnish composition; and exposing the cured whitening varnish composition to light to accelerate the bleaching process, wherein the surface to be lighted is imaged prior to lighting, and the image is used to adapt the exposure area of the lighting.

BRIEF DESCRIPTION OF THE DRAWINGS

FIGS. 1 and 2 are schematic drawings of embodiments of a system according to the invention.

DETAILED DESCRIPTION OF THE INVENTION

Figure 1:
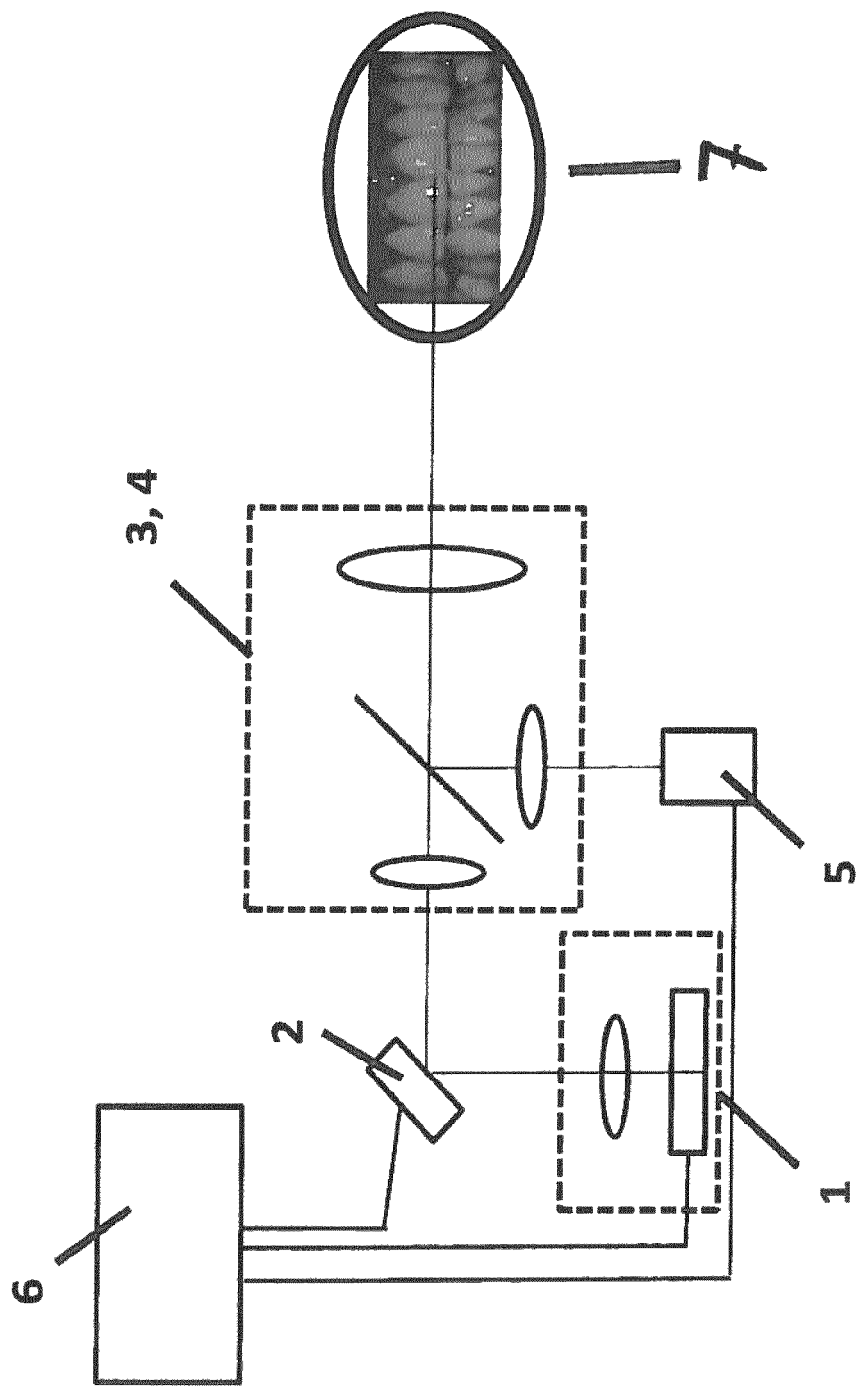

In a general sense, the invention is based on the judicious insight that using a smart lighting system can greatly enhance the soft-tissue saving benefits of a light activated tooth whitening varnish. Additionally, the smart lighting system of the invention can also be beneficial in the event of conventional whitening using high concentrations of hydrogen peroxide. The invention particularly pertains to extraoral systems. I.e., systems that are themselves not introduced into the mouth, but which are to be operated outside of the mouth, with the emitted light entering the mouth.

When making use of tooth whitening varnish with light activation, soft tissue is heated by the light. E.g., for blue LED light at 465 nm, the desired safe exposure would typically be below 50 mW/cm2. However, for efficient whitening, it would be desirable to use 100-200 mW/cm2. The invention serves to avoid soft tissue masking by applying light only to the tooth. The presentation of the tooth whitening agent in the form of a varnish, serves to lock the agent on the tooth, thereby preventing soft tissue from becoming chemically irritated. In lieu of a varnish, also a gel can be used with the light system of the invention, if the concentration is low, e.g., below 10%, or if the gel is carefully painted on the teeth and not disturbed during the time that it is present thereon.

The system will generally comprise components or units having one or more of the following functions.

a) Light generation: typically, one or more Light Emitting Diodes (LEDs) or a laser are employed for generating light. To this end, the system comprises a light-generating unit (1), i.e., a unit that generates and emits light; this unit comprises a light source, and is typically a light-emitting diode (LED) or a laser; typically the light-generating unit is adapted to emit light of wavelength 300 to 1100 nm, such as LED or laser light of wavelength 400 to 850 nm, preferably 400-500 nm, e.g. 465 nm. It is noteworthy that, as a result of the present invention, the low end of the wavelengths. e.g. below 420 nm can be more easily used, and by virtue of the invention even shorter wavelengths, into UV, are less prone to safety issues, and can thus be used, with the added benefit of a more efficient whitening process, i.e. a faster result.

b) Light patterning: this refers to creating a modulated light beam with the light, which can be projected onto a surface to generate a spatially varying light pattern or image; i.e. subjecting the light to a varying modulation depending on the angle or spatial position of the light within the light beam. Spatial light modulation is well-known to the skilled person. It generally implies passing a light beam through a modulating device which provides a different modulation depending on the position at which the light passes through the device, or reflecting the light from the surface of a modulating device where the angle of the light reflected from the surface depends on the position at which the light strikes the device; Accordingly, the intensity of the light rays within the beam of light projected onto the teeth, varies with their spatial position and angle within the overall light beam.

Thereby the light can be spatially modulated by passing the beam of light through a spatial light modulator (which could for example comprise a liquid crystal device or a DLP [Digital Light Processing] device). In the case of a narrow beam light source such as a laser it would also be generally desirable to deflect the source beam over a range of angles to form a broader spatially varying beam. To this end, the system of the invention comprises a light-patterning unit (2); this unit serves to generate the spatial variation of the light pattern formed on the surfaces to be illuminated; the light-patterning unit can be a separate unit, but it can also be integrated with the light-generating unit; in the latter case, the light-patterning unit can also be provided in the form of a spatially adjustable light source, whereby the light emitted by the light-generating unit can thus be turned into one or more desired directions (up, down, left, right). The light-patterning unit can also be a combination of a spatially adjustable light source and a separate set of one or more mirrors and/or one or more lenses; Light generation and light patterning can be provided by separate components, but combined light generation and light patterning can be provided by a single pixelated light source, for example an array of LEDs which are individually controllable to have different brightness.

c) Light projection: the spatially varying light beam is projected so that it forms a focussed spatially varying light pattern at the position of the mouth. This can be performed, e.g., using a system of lenses and/or mirrors which control the overall size of the light pattern and ensure that it is focussed at the teeth. To this end, the system of the invention comprises a light-projection unit (3).

d) Mouth imaging: hereby an image of the mouth is formed on an imaging device by an appropriate camera lens. Light projection and mouth imaging can be provided by separate components, but the projection of the light pattern and formation of the image on the sensor can also be combined, e.g., in a system of lenses and mirrors. The mirrors can have wavelength dependent characteristics (e.g. dichroic mirrors).

e) Mouth image sensing: an image sensor is a device that converts an optical image into an electronic signal. It is known to the skilled person from the field of digital cameras, camera modules and other imaging devices. Early analogue sensors were video camera tubes; currently used types are semiconductor charge-coupled devices (CCD) or active pixel sensors in complementary metal-oxide-semiconductor (CMOS) or N-type metal-oxide-semiconductor (NMOS, Live MOS) technologies. Generally, mouth imaging and mouth image sensing will be provided by an imaging device, such as a digital camera comprising a CCD or CMOS sensor, to convert the image of the mouth into mouth image data.

The system of the invention comprises a mouth imaging unit (4); this unit, typically in conjunction with a mouth image sensing unit (5), such as a CCD or CMOS sensor as discussed above, serves to render an image of the area to be covered by lighting; typically this unit comprises a camera, so as to make an optically visible image; the imaging unit, however, can also be any other unit capable of scanning an area, e.g. by various forms of electromagnetic radiation other than light, and rendering an image based on the scanned area; the imaging unit typically is a separate unit, but it can also be integrated with the light-projecting unit, e.g. using the lens of the camera also as a lens for directing the emitted light; the imaging unit can also be integrated with any other of the units; preferably, the imaging unit is capable of operating on the basis of wavelengths that are different from the wavelengths of the light-generating unit, and preferably at wavelengths that are not prone to cause damage to soft tissue; preferably, the imaging unit, particularly the camera and associated imaging software, operates at wavelengths where there is a large difference in reflectivity of the teeth and the gums; to this end the preferred wavelengths are shorter than approximately 625 nm, such as shorter than 600 nm (particularly yellow-green-blue-violet). A combination of wavelengths (including red) can be used in order to generate an image in which the teeth and gums can be easily differentiated.

Arranging that the imaging unit operates on the basis of wavelengths that are different from the wavelengths of the light-generating unit, judiciously avoids saturating the image sensor with high intensity light. It will be understood that hereby the wavelength for the imaging unit can be higher or lower than that of the light-generating unit. In this preferred embodiment, the wavelengths for the imaging unit and the wavelengths emitted by the light-generating unit can be different, but still within the same preferred range.

The wavelengths for the imaging unit are preferably at least 400 nm, and more preferably above 410 nm. The preferred upper limit of 625 nm serves to ensure generating good contrast between teeth and gums.

f) Image processing and control: the mouth image data is analysed and used to control the spatially varying light beam. The system of the invention comprises an image processing and control unit (6); the image processing and control unit typically is a data processing unit, a CPU (central processing unit), or any other unit capable of receiving and processing data; in the system of the invention, the image processing and control unit serves to adjust the light-patterning unit on the basis of information, typically an image, obtained from the imaging unit; this adjustment typically is done prior to allowing the light-generating unit to emit light, as this will prevent the light from affecting undesired areas, such as soft tissue. The image processing and control unit can be a separate unit, but it can also be integrated with one or more of the other units of the system of the invention. Particularly, the image processing and control unit can be integrated with the imaging unit (from which it receives the imaging data to be processed), the light-patterning unit (which it is to adjust on the basis of the imaging data as processed), or both.

It will be understood that any one combination of two or more of the aforementioned units, including all of the units, can be integrated. The fact that units are integrated generally means that such units are part of a single device, or contained on a single platform. It will also be understood that the aforementioned units have the appropriate optical and electrical connections to each other. Suitable connections, and suitable software to operate the system, are in itself standard items in the art, and do not require elucidation here.

Optionally, but preferably, the system of the invention also comprises a lip retractor. The lip retractor is a known device for use in tooth treatments such as tooth whitening. It initially serves its conventional purpose, viz. to prevent the lips from coming into contact with the whitening composition, particularly as it cures, and to optimally expose the tooth surface to the treatment. In the system of the invention, the presence of a lip retractor also provides an additional benefit, in that it can be advantageously used as a reference frame for the imaging unit, as it helps to define the area to be imaged and/or it can serve as a focusing aid.

The smart lighting system is schematically illustrated with reference to FIGS. 1 and 2. It will be understood that the invention is not limited to the embodiments shown in any of the figures. Accordingly, the following description, whilst discussing the components shown in FIG. 1, is also applicable to other embodiments, not necessarily as shown. Said components are in direct or indirect communication with each other; the skilled person will understand, as a result of their stated functions, how these components interact with each other.

In a typical embodiment as shown in FIG. 1, the smart lighting system of the invention operates as follows. It images the teeth using a camera (typically a digital camera comprising a mouth imaging unit (4) and a mouth image sensing unit (5) operating, possibly using a lip refractor as a reference frame for image area and focus. Image processing software determines the area of the teeth, for example, by thresholding the colour and intensity data. Blue light from a LED source, i.e. a light-generating unit (1), is projected back onto the teeth (optionally through the same optics as the camera) via a DLP array or similar (as is used in digital projectors), shown as the light patterning unit (2, and the image of the teeth is used to create a mask pattern which is supplied to the DLP. Again the lip retractor may be used for auto-alignment. The camera (4,5) and DLP (2) can be used in 'real time' to adjust for any movements, and the light source can be varied in intensity according to a timed programme, or for example can be reduced or shut down if movements are severe or the image is changed or obstructed.

Optionally, a beam splitter is provided, thus enabling the camera and the projector to share the same output path. Preferably, the camera and image processing software work at wavelengths where there is a large difference in reflectivity of teeth and gums (generally less than about 650 nm) and wavelengths different from the intense blue light source which could swamp the image.

In FIG. 1 the projection of the light pattern, using the light-projection unit (3) and the formation of the image on the sensor, using the mouth imaging unit (4) are combined in a system of lenses and mirrors.

In FIG. 2, a set-up is shown wherein the functions of light projection and imaging are separated. Therein a mouth imaging unit (4) together with a mouth image sensing unit (5) renders an image of the mouth, which image is processed by an image processing and control unit (6). The latter unit serves to adjust a light-patterning unit (2), so as to have a light projecting unit (3) project light as emitted by a light-generating unit (1), onto a desired area of the mouth (7).

The smart lighting system preferably produces incident intensities of up to 200 mW/cm2.

The image processing serves to calculate the area of the teeth and if required adjust the LED source to give the right power density. The distance between the smart lighting system and the teeth can be fixed, or it can be adjustable based on a measurement by an auto-focusing system. The system of the invention preferably does not require operator adjustment or calibration. Optionally, a test lip retractor with dummy teeth can be provided.

The invention also pertains to a cosmetic method (i.e., a non therapeutic method) for light-activated tooth whitening. The method comprises the steps of: applying a curable whitening varnish composition containing a bleaching agent to the surface of a tooth; curing the whitening varnish composition; and exposing the cured whitening varnish composition to light to accelerate the bleaching process. In accordance with the invention, the surface to be lighted is imaged prior to lighting, and the image is used to adapt the exposure area of the lighting. Hereby it is preferred to use the system described hereinabove. It will be understood that the invention also includes the system as described hereinbefore and hereinafter, in all its embodiments, for use in said cosmetic method.

The foregoing particularly concerns a cosmetic method for the whitening of a pre-cleaned tooth surface (or pre-cleaned teeth surfaces). Cleaning generally implies the removal of dental plaque and/or biofilm. This is customary in teeth whitening procedures, particularly in in-office teeth whitening procedures conducted by professionals. I.e., the bleaching itself works to have a cosmetic effect, it does not itself work as a therapy to remove dental plaque or bio film; Also, it will be understood (particularly in the context of the present invention, which allows the precise targeting of surfaces to be treated), that the teeth whitening according to the invention occurs on the enamel surfaces of teeth, not in the areas between the teeth or along the cervical margins, where dental plaque is mostly found. In any of its embodiments.

In an embodiment of this method, the following steps occur: first a lip retractor is inserted into the mouth, as is usually done in the teeth whitening methods; a teeth whitening varnish is painted onto the teeth and dried. Different from conventional teeth whitening, the steps of soft tissue masking prior to gel application are not necessary. The smart light system as described above is brought to the tooth and applied (e.g., for 5 to 45 minutes, typically for 10 to 20 minutes, particularly for 15 minutes, but shorter and longer times are conceivable). The steps of applying the varnish and applying the light can be repeated (e.g., 3 to 4 times), as desired to complete the whitening process.

The method of the invention is of particular benefit for tooth whitening in a professional, "in office" context. This is particularly in view of the great benefits that the invention brings about in terms of preventing soft tissue to be affected, as compared to conventional whitening in the event of using high concentrations of hydrogen peroxide (e.g. 25%), which typically is a professional treatment. Also the equipment making up the system of the invention would be more economically and more advantageously be applied in a professional's office, rather than at home. Nevertheless, considering the extent of size reduction at present available for light emitting devices, such as LED's, for digital camera's, and for image processing units, it is conceivable to integrate the various unit into a home-size equipment. Particularly since the system of the invention allows using a method that, if conducted properly, is not prone to affect soft tissue, the invention does have the benefit of being better applicable by lay persons, e.g. at home, than conventional systems when using high concentrations of hydrogen peroxide.

Further aspects of the method of the invention, and the whitening varnish used, are essentially the same as disclosed in the aforementioned WO 2014/97053, the disclosure of which is incorporated herein by reference.

Particularly, a whitening varnish composition and an optional barrier layer can thereby be applied to the teeth of a person, to whiten the teeth. The composition 10 may be applied by a dental professional, such as a dentist, or by the wearer. The whitening varnish composition can be applied to the teeth using, e.g., an applicator, such as a pen, brush, piece of foam, or a cloth applicator to form a layer. In other embodiments, the composition may be inserted into an applicator, such as a dental tray, which is positioned adjacent the teeth and then removed. This can be after partial curing of the whitening varnish composition, after which the further curing is conducted using the system and method of the present invention.

The whitening varnish composition 10 may be applied to the teeth at a thickness of, for example, from 10-500 μm, such as from 10-100 μm, e.g., about 50 μm. Optionally, a barrier layer is applied over the layer of the whitening composition.

The whitening varnish composition is then cured or otherwise hardened to form a film containing the bleaching agent on the teeth. The curing/hardening may be performed with light, moisture, solvent evaporation, or a combination of these. In one embodiment, the varnish comprises a matrix material that includes a resin component which is moisture-cured, for example, by saliva naturally present on the teeth. In another embodiment, the matrix material includes a solvent which evaporates. In yet another embodiment, the resin component of the matrix material includes a curing agent and is cured by light, such as blue light, from a suitably positioned light source. In the present invention, the above-described system, which particularly serves to provide the light assisting the bleaching process, can also be used for providing the light if such is used for curing. This is of particular benefit in the event that the curing is by blue light, particularly in the event that the curing takes relatively long. For compositions which take minutes or longer to cure, soft tissue in the mouth, such as the lips and/or gums, are preferably held away from the teeth, e.g., with a lip retractor, and preferably the smart lighting system of the invention is used. The optional barrier layer can be cured contemporaneously with the whitening varnish composition, or it can be applied subsequently and cured or allowed to cure separately.

Next, the bleaching agent in the cured whitening varnish composition is activated by the application of light energy. The light energy enhances the chemistry of interaction between bleaching agent and stains on the user's teeth. The light is applied by the smart lighting system as discussed above. Incoherent or coherent light may be used for this step of the process, for example, LED or laser light of wavelength 300 to 1100 nm, such as LED or laser light of wavelength 400 to 850 nm, e.g., LED or laser light of wavelength of 540 to 700 nm. In exemplary embodiments, light energy in the visible spectrum of between 400 and 700 nm is applied to the varnish-covered teeth. The laser may be chosen to provide a wavelength tailored to the colour of the stain molecules so that the energy of the laser is largely absorbed by the stains rather than by the tooth tissues. The application of light energy may be maintained for a treatment period of, for example 3 to 300 minutes, such as 15 to 180 minutes, e.g., for about 30 to 120 minutes. Illumination of the stained teeth may be performed individually tooth by tooth, in small groups of teeth, or simultaneously on all teeth as a whole. The light emerging from the light source may be continuous ("on" the entire procedure), interrupted continuous (primary "on" with short rest interruptions), pulsed ("on" and "off" in a predetermined timed sequence and intensity), or a combination of continuous, interrupted continuous and pulse.

In exemplary embodiments from about 25 to about 200 mW/cm$^2$ of light is applied continuously to the surface of the teeth. In an exemplary embodiment, bleaching of stained teeth is achieved using an argon ion laser to light activate the bleaching agent. In the visible spectrum, argon produces blue and green light with a wavelength in the range of 450-530 nm. In an exemplary embodiment, 465 nm blue light is applied at a power density of 25 to 200 mW/cm$^2$. In an exemplary method, after the dental professional (e.g., dentist) applies the varnish composition, the dentist or other dental professional applies, using the system of the invention, strong blue light for a period of time (for example, 1 to 2 hours), chair-side. This may comprise a single treatment, or a multiplicity of shorter applications of varnish and light during the 2 hour chair time. After application of light treatment, the patient may leave the office of the dental professional and the varnish is left on the patient's teeth and continues to whiten after the patient has left the office of the dental professional. This will continue until the varnish is removed at some later time. In exemplary embodiments, the patient may intermittently accelerate further with a portable light emitting mouthpiece at home, whilst the varnish remains intact. It is generally possible, at the end of the treatment period, to remove the composition from the teeth by peeling it away from the teeth and/or by brushing the teeth. In embodiments, the whitening varnish composition remains on the tooth for a period of time ranging from about 30 minutes to about 10 hours after the termination of light treatment. The process may be repeated, for example, once or twice a day, week, or month or less frequently, until a desired colour change is effected or to maintain whiteness of the teeth.

In embodiments, the cured whitening varnish composition is exposed to light in one or more treatments for a total light exposure time in the range of from about 10 minutes to about 120 minutes. In embodiments, light with a wavelength in the range of about 400 nm to about 500 nm is applied to the cured whitening varnish composition to accelerate the bleaching process. In embodiments, the cured whitening varnish composition is exposed to light four times, and in each of the four times from about 25 to about 200 mW/cm$^2$ of light is applied to the cured whitening varnish composition for a period of about 15 minutes to accelerate the bleaching process, for a total light exposure time of about 60 minutes.

It will be clear from the above, that light may be applied for two different purposes; namely, to cure the whitening varnish composition (if the varnish is light-curable) and to accelerate the bleaching process. The light-application parameters for the curing step may be different from the parameters for the bleaching acceleration step. Typically, light curing requires only a short exposure (e.g., 30 seconds to 3 minutes) and bleaching acceleration typically requires somewhat longer exposures (e.g., 10 minutes to 120 minutes).

The whitening varnish composition 10 includes a dental bleaching agent. Exemplary bleaching agents are solid at ambient conditions and include carbamide peroxide, which is an adduct of urea and hydrogen peroxide ($CH_4N_2O$—$H_2O_2$). This material releases hydrogen peroxide on contact with water. Other example bleaching agents include alkali metal percarbonates, sodium perborate, potassium persulfate, calcium peroxide, zinc peroxide, magnesium peroxide, strontium peroxide, other hydrogen peroxide complexes, sodium chlorite, combinations thereof, and the like. The term "bleaching agent," herein refers to compounds which are themselves bleaches and to compounds which are bleach precursors, such as carbamide peroxide, which react or decompose to form a bleach, such as hydrogen peroxide. The whitening varnish composition can include the bleaching agent, e.g., carbamide peroxide, at a concentration of at least 5 wt. % or at least 10 wt. %, such as up to about 95 wt. %, or up to about 60 wt. %. 20 wt. % carbamide peroxide, as an example, corresponds to a hydrogen peroxide concentration per particle of about 6 wt. %. Higher concentrations of the bleaching agent may be employed to achieve an overall concentration in the whitening varnish composition 10 of at least 2 wt. % or more, as noted above.

In embodiments, the varnish contains up to 30% hydrogen peroxide when cured. Such compositions formulated with carbamide peroxide may result the release of a level of urea upon contact with water sufficient to impact the properties of the varnish, such as viscosity and cure time. Accordingly, in lieu of carbamide peroxide, such compositions may be formulated using aqueous hydrogen peroxide, such as a solution of 60% hydrogen peroxide in 40% water. Exemplary Varnish Compositions.

Suitable whitening varnish composition 10 include self-cured (e.g. by solvent evaporation) and light-cured compositions. For the components of the whitening varnish, and for illustrative compositions of the whitening varnish, reference is made to the extensive disclosure thereof in WO 2014/097053.

The bleaching agent preferably is hydrogen peroxide at a concentration range of 1-25%. In an interesting embodiment, the concentration is 15-25%, typically 20%, for professional use or 5-10%, typically 8% for at home use. In jurisdiction with a tighter regulation, the percentage can be lower, e.g. 2-5%, typically 3.75%, for at home use in the EU.

In order to improve the removability of the varnish, after hardening under the influence of light, it is preferred to include softeners such as propylene glycol or dipropylene glycol, typically in an amount of 10-20 wt %. When doing so, it is recommendable to maintain the desired viscosity by reducing the polymer matrix in proportion.

The invention also pertains to a kit for the whitening of teeth, said kit comprising a system as described above, in any of its embodiments, and a supply of curable whitening varnish, in any of its embodiments described above. The supply of curable varnish will, e.g., be in the form of a container comprising the varnish. The container can, e.g., be a box, a tube, and it may be in a one component form or in plural component form, typically two components. Such components can packed separately, in which case the supply of curable varnish comprises more than package, such as more than one container.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein feedback from the image processing and control unit is employed to manually set the light-patterning unit.

In an interesting alternative embodiment, measures are taken to improve directing light also to teeth at the sides of the mouth, which are more prone to be in shadow, particularly in the interproximal spaces. This serves to enhance the uniformity of the whitening. To this end two projectors or two projection lenses can be arranged to illuminate the left and right sides of the mouth. Further, the intensity of the light at the edges of the projected light pattern can be graded, so as to avoid a sharp boundary, which might result in a step change in tooth colour. This grading can be implemented in a number of ways, e.g., by grading the intensity, by spatial dithering or by temporal dithering.

In yet another embodiment, image processing requirements are simplified by projecting a scanning spot onto the teeth/gums. This is typically done periodically (for example when significant movement of the patient is detected). A benefit comes from the fact that for each projected pixel (spot position) it is possible to detect whether it falls on tooth or gum. This avoids having to relate the positions of pixels in the images recorded by the camera/cameras to the position of pixels in the projected image. Instead of using a spatial light modulator to generate a dynamic light pattern it is also possible to use a custom printed mask pattern generated from a camera image.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

In sum, we hereby disclose a smart lighting system for applying light to teeth in the context of tooth whitening. This particularly concerns teeth that have been provided with a light-curable whitening varnish. The system comprises a light-generating unit, a light-patterning unit, a mouth imaging unit, a mouth image sensing unit, and an image processing and control unit, and is adapted so as to allow the image processing and control unit to adjust the light-patterning unit on the basis of information obtained from the mouth image sensing unit. By doing so, prior to allowing the light-generating unit to emit light, it can be ensured that light emitted to assist tooth whitening, does not affect soft tissue.

The invention claimed is:

1. A system, for applying light of a desired high intensity to teeth, the system comprising a light-generating unit arranged to generate light, a light-patterning unit comprising a spatial light modulator configured to create a spatially modulated light beam, a light projection unit arranged to project the spatially modulated light beam as a projected light pattern, a mouth imaging unit arranged to form an image of the mouth b a camera lens, a mouth image sensing unit arranged to convert the image into an electrical signal, and an image processing and control unit arranged to analyze image data to calculate an area of the teeth and control the spatially modulated light beam, said light-generating unit, said light-patterning unit, said light projection unit, said mouth imaging unit, said mouth image sensing unit, and said image processing and control unit in communication with each other, wherein two or more of these units are optionally combined as a single component; the system being adapted so as to allow the image processing and control unit to adjust the light-generating unit or the light-patterning unit on a basis of the image captured by the mouth imaging unit, prior to allowing the light-generating unit to emit light of the desired high intensity, wherein the light-patterning unit is integrated with the light-generating unit and the light-patterning unit is a spatially adjustable light source, whereby the light emitted by the light-generating unit can be turned in one or more directions.

2. A cosmetic method for light-activated tooth whitening, the method comprising the steps of:

applying a curable whitening varnish composition containing a bleaching agent to a surface of at least one tooth;

curing the curable whitening varnish composition; and exposing, with a system, the cured whitening varnish to light to accelerate a bleaching process, the system comprising a light-generating unit arranged to generate light, a light-patterning unit comprising a spatial light modulator configured to create a spatially modulated light beam, a light projection unit arranged to project the spatially modulated light beam, a mouth imaging unit arranged to form an image of the mouth by a camera lens, a mouth image sensing unit arranged to convert the image into an electrical signal, and an image processing and control unit arranged to analyze image data to calculate an area of the teeth and control the spatially modulated light beam in communication with each other, wherein the light-generating unit or the light-patterning unit is adapted on a basis of the image captured by the mouth imaging unit to adjust at least a power density of light emitted from the light-generating unit prior to lighting, and an image is used to adapt an exposure area of the lighting, and wherein the light-patterning unit is integrated with the light-generating unit and the light-patterning unit is a spatially adjustable light source, whereby the light emitted by the light-generating unit can be turned in one or more directions.

3. A system for applying light of a desired high intensity to teeth, the system comprising a light-generating unit arranged to generate light, a light-patterning unit comprising a spatial light modulator configured to create a spatially modulated light beam, a light projection unit arranged to project the spatially modulated light beam as a projected light pattern, a mouth imaging unit arranged to form an image of the mouth by a camera lens, a mouth image sensing unit arranged to convert the image into an electrical signal, and an image processing and control unit arranged to analyze image data to calculate an area of the teeth and control the spatially modulated light beam, said light-generating unit, said light-patterning unit, said light projection unit, said mouth imaging unit, said mouth image sensing unit, and said image processing and control unit in communication with each other, wherein two or more of these units are optionally combined as a single component; the system being adapted so as to allow the image processing and control unit to adjust the light-generating unit or the light-patterning unit on a basis of the image captured by the mouth imaging unit, prior to allowing the light-generating unit to emit light of the desired high intensity wherein the light-generating unit and the light-patterning unit are provided by a single pixelated light source, and wherein the single pixelated light source comprises an array of LEDs that are individually controllable to have different brightness.

4. A system for applying light of a desired high intensity to teeth, the system comprising a light-generating unit arranged to generate light, a light-patterning unit comprising a spatial light modulator configured to create a spatially modulated light beam, a light projection unit arranged to project the spatially modulated light beam as a projected light pattern, a mouth imaging unit arranged to form an image of the mouth by a camera lens, a mouth image sensing unit arranged to convert the image into an electrical signal, and an image processing and control unit arranged to analyze image data to calculate an area of the teeth and control the spatially modulated light beam, said light-generating unit, said light-patterning unit, said light projection unit, said mouth imaging unit, said mouth image sensing unit, and said image processing and control unit in communication with each other, wherein two or more of these units are optionally combined as a single component; the system being adapted so as to allow the image processing and control unit to adjust the light-generating unit or the light-patterning unit on a basis of the image captured by the mouth imaging unit, prior to allowing the light-generating unit to emit light of the desired high intensity, wherein light at the edges of the projected light pattern is graded and the light is graded by grading the intensity of the light, spatial dithering, or temporal dithering.

\* \* \* \* \*